US009833398B2

(12) United States Patent
Hakozaki et al.

(10) Patent No.: US 9,833,398 B2
(45) Date of Patent: Dec. 5, 2017

(54) METHOD OF TREATING A SKIN CONDITION AND COMPOSITIONS THEREFOR

(71) Applicant: The Procter & Gamble Company, Cincinnati, OH (US)

(72) Inventors: Tomohiro Hakozaki, Cincinnati, OH (US); John Erich Oblong, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/402,332

(22) Filed: Jan. 10, 2017

(65) Prior Publication Data

US 2017/0196795 A1 Jul. 13, 2017

Related U.S. Application Data

(60) Provisional application No. 62/277,181, filed on Jan. 11, 2016.

(51) Int. Cl.
| | |
|---|---|
| *A61K 8/18* | (2006.01) |
| *A61K 8/67* | (2006.01) |
| *A61K 8/60* | (2006.01) |
| *A61K 8/36* | (2006.01) |
| *A61Q 19/00* | (2006.01) |
| *A61Q 17/04* | (2006.01) |
| *A61Q 19/02* | (2006.01) |

(52) U.S. Cl.
CPC .............. *A61K 8/675* (2013.01); *A61K 8/361* (2013.01); *A61K 8/60* (2013.01); *A61Q 17/04* (2013.01); *A61Q 19/00* (2013.01); *A61Q 19/02* (2013.01); *A61K 2800/48* (2013.01)

(58) Field of Classification Search
CPC ........ A61K 35/16; A61K 35/60; A61K 36/16; A61K 36/23; A61K 36/31; A61K 38/05; A61Q 19/007; A61Q 17/005; A61Q 1/00; A61Q 19/06; A61Q 17/04; A61Q 5/00; A61Q 7/00
See application file for complete search history.

(56) References Cited

U.S. PATENT DOCUMENTS

| | | | |
|---|---|---|---|
| 5,053,230 | A | 10/1991 | Gazzani |
| 5,833,998 | A | 11/1998 | Biedermann et al. |
| 5,968,528 | A | 10/1999 | Deckner et al. |
| H2013 | H | 2/2002 | Boyd et al. |
| 8,106,184 | B2 | 1/2012 | Sauve |
| 8,197,807 | B2 | 6/2012 | Brenner |
| 8,383,086 | B2 | 2/2013 | Brenner |
| 8,933,217 | B2 | 1/2015 | Rinsch et al. |
| 8,999,923 | B2 | 4/2015 | Cao et al. |
| 2002/0022052 | A1* | 2/2002 | Dransfield ........... A61K 9/0014 424/449 |
| 2003/0032617 | A1 | 2/2003 | Harel et al. |
| 2005/0176677 | A1 | 8/2005 | Dal Farra et al. |
| 2005/0227327 | A1 | 10/2005 | Brenner |
| 2005/0267023 | A1 | 12/2005 | Sinclair |
| 2006/0040851 | A1 | 2/2006 | Ghosh |
| 2006/0229265 | A1 | 10/2006 | Milburn |
| 2007/0027095 | A1 | 2/2007 | Brenner |
| 2007/0231288 | A1 | 10/2007 | Arnaud et al. |
| 2008/0025932 | A1 | 1/2008 | Bissett et al. |
| 2008/0312169 | A1 | 12/2008 | Johnson et al. |
| 2009/0196942 | A1 | 8/2009 | Goyarts |
| 2010/0015072 | A1 | 1/2010 | Polla |
| 2010/0040608 | A1 | 2/2010 | Wahren-Herlenius et al. |
| 2011/0101021 | A1 | 5/2011 | Greer |
| 2011/0262560 | A1 | 10/2011 | Dabe et al. |
| 2012/0003168 | A1 | 1/2012 | Lyga et al. |
| 2012/0022013 | A1 | 1/2012 | Sinclair |
| 2012/0121534 | A1 | 5/2012 | Thorel et al. |
| 2012/0172584 | A1 | 7/2012 | Sauve |
| 2012/0225050 | A1 | 9/2012 | Knight et al. |
| 2013/0319449 | A1 | 12/2013 | Xavier et al. |
| 2014/0065099 | A1 | 3/2014 | Alvarez et al. |
| 2014/0090660 | A1 | 4/2014 | Xavier et al. |
| 2014/0127332 | A1 | 5/2014 | Bider |
| 2014/0170195 | A1 | 6/2014 | Fassih et al. |
| 2014/0190507 | A9 | 7/2014 | Xavier et al. |
| 2014/0328775 | A1 | 11/2014 | Laughlin, II |
| 2016/0077080 | A1 | 3/2016 | Laughlin, II |
| 2016/0235646 | A1 | 8/2016 | Shah et al. |

(Continued)

FOREIGN PATENT DOCUMENTS

| | | |
|---|---|---|
| CN | 102 871 863 | 4/2014 |
| EP | 3 040 065 A1 | 7/2016 |

(Continued)

OTHER PUBLICATIONS

International Search Report and Written Opinion of the International Searching Authority, PCT/US2017/012786, dated Mar. 20, 2017, 13 pages.
A.B. Kimball et al., Reduction in the appearance of facial hyperpigmentation after use of moisturizers with a combination of topical niacinamide and N-acetyl glucosamine: results of a randomized, double-blind, vehicle-controlled trial, British Journal of Dermatology 2010, vol. 162, No. 2, pp. 435-441.
International Search Report and Written Opinion PCT/US2016/029951 dated Aug. 23, 2016, 11 pages.
International Search Report and Written Opinion PCT/US2016/039926 dated Aug. 22, 2016, 11 pages.
Ebanks Jody P et al: "Mechanisms regulating skin pigmentation: the rise and fall of complexion coloration.", International Journal of Molecular Sciences Sep 2009, vol. 10. No. 9, Sep. 2009.
Ferrza, J. et al. "Kinetic a-Deuterium Isotope Effects for Enzymatic and Nonenzymatic Hydrolysis of Nicotinamide-β-Riboside" Archives of Biochemistry and Biophysics vol. 191, No. 2, Dec. pp. 431-436, 1978, 6 pages.

(Continued)

*Primary Examiner* — Nannette Holloman
(74) *Attorney, Agent, or Firm* — John G. Powell (57) ABSTRACT

Cosmetic methods and compositions for improving the appearance and barrier function of skin. The methods and compositions utilize a combination of niacinamide and a suitable saccharide at low pH to decrease trans-epidermal water loss in skin, reduce the size of hyperpigmented spots, and improve the appearance of skin better than their high pH counterparts.

19 Claims, 4 Drawing Sheets

(56) References Cited

U.S. PATENT DOCUMENTS

| | | |
|---|---|---|
| 2016/0250241 A1 | 9/2016 | Deren-Lewis |
| 2016/0317418 A1 | 11/2016 | Hakozaki et al. |
| 2016/0317419 A1 | 11/2016 | Hakozaki et al. |
| 2016/0317420 A1 | 11/2016 | Hakozaki et al. |
| 2016/0374908 A1 | 12/2016 | Hakozaki et al. |
| 2016/0374918 A1 | 12/2016 | Dihora et al. |
| 2016/0374919 A1 | 12/2016 | Hakozaki et al. |
| 2017/0121746 A1 | 5/2017 | Velasquez et al. |

FOREIGN PATENT DOCUMENTS

| | | |
|---|---|---|
| FR | 2 845 596 A1 | 4/2004 |
| FR | 2 975 295 A1 | 11/2012 |
| GB | 2 472 379 A | 2/2011 |
| WO | WO 00/71093 A1 | 11/2000 |
| WO | WO 2006/127987 | 11/2006 |
| WO | WO 2011/074143 A1 | 6/2011 |
| WO | WO 2015/061512 | 4/2015 |
| WO | WO 2015/186114 | 12/2015 |
| WO | WO 2016/034519 A1 | 3/2016 |
| WO | WO 2016/188691 A1 | 12/2016 |

OTHER PUBLICATIONS

Oppenheimer, N. "NAD Hydrolysis: Chemical and Enzymatic Mechanisms" Molecular and Cellular Biochemistry 138: 245-251, 1994.
Hakozaki T et al: "The effect of niacinamide on reducing cutaneous pigmentation and suppression of melanosome transfer", British Journal of Dermatology, Oxford: Wiley-Blackwell, UK, vol. 147. No. 1, Jul. 1, 2002.
International Search Report PCT/US2016/029943; dated Jul. 1, 2016; 19 pages.
International Search Report PCT/US2016/029945; dated Jun. 27, 2016; 15 pages.
International Search Report PCT/US2016/039924; dated Aug. 26, 2016; 11 pages.
International Search Report PCT/US2016/039925; dated Aug. 25, 2016; 11 pages.
Sinthupoom Nujarin et al: "Nicotinic acid and derivatives as multifunctional pharmacophores for medical applications", European Food Research and Technology, Springer Verlag. Heidelberg. DE. vol. 240, No. 1. Oct. 29, 2014 (Oct. 29, 2014). pp. 1-17.
U.S. Appl. No. 62/155,672, filed May 1, 2015, Tomohiro Nmn Hakozaki et al.

* cited by examiner

METHOD OF TREATING A SKIN CONDITION AND COMPOSITIONS THEREFOR

FIELD

The present disclosure is directed generally to a method of providing a skin health and/or appearance benefit and compositions therefor. More specifically, the present disclosure is directed to methods and compositions that utilize a combination of niacinamide and ribose at low pH to provide a skin benefit.

BACKGROUND

Skin is the first line of defense against environmental insults that would otherwise damage sensitive underlying tissue and organs. For example, skin maintains a relatively water-impermeable barrier between an organism and its environment to prevent dehydration. Additionally, skin plays a key role in a person's physical appearance. Generally, most people desire to have younger, healthy looking skin. And to some of these people, the tell-tale signs of skin aging such as thinning skin, wrinkles, and age spots are an undesirable reminder of the disappearance of youth.

Both intrinsic and extrinsic factors can lead to a decline in skin appearance and function. For example, as skin ages naturally, there is typically a reduction in the cells and blood vessels that supply the skin and a flattening of the dermal-epidermal junction, which leads to thinning and general degradation of the skin's barrier function. Additionally, lifestyle choices and exposure to the environment (e.g., ultraviolet radiation, pollution, cigarette smoke, smog, wind, heat, low humidity, harsh surfactants, abrasives) may lead to the premature appearance of age spots and uneven skin tone. As a result, treating the signs of aging in skin has become a booming business in youth-conscious societies. Treatments range from cosmetic creams and moisturizers to various forms of cosmetic surgery.

Numerous agents, both natural and synthetic, are known for use in skin care compositions marketed to treat various skin conditions, especially those associated with aging. One example of a well-known skin care agent is niacinamide, which has been used in the cosmetics industry to provide a variety of skin health benefits. For example, U.S. Pat. No. 5,833,998 discloses the use of niacinamide for regulating the oily/shiny appearance on skin, and U.S. Pat. No. 5,968,528 discloses the use of niacinamide for regulating the signs of skin aging.

Other examples of well-known skin care agents include saccharides (mono and poly), which have also been widely used in the cosmetics industry to provide a variety of skin health benefits. For example, US 2005/0176677 discloses that mono- and polysaccharides derived from plants of the Lemnaceae family provide various skin care benefits. In another example, US 2008/0312169 discloses the use of D-ribose in a cosmetic composition applied to the skin to reduce the length and area of wrinkles and to improve the complexion of the skin.

In some instances, the combination of skin agents such as niacinamide and saccharides have been disclosed in exemplary cosmetic compositions. For example, US 2012/0121534 and U.S. Pat. No. 5,053,230 disclose compositions for promoting the growth of skin cells to improve the appearance of wrinkled skin. The compositions in the '534 application and '230 patent are disclosed as essentially being growth media for stimulating growth or promoting trophism in skin cells. Some of the examples in these publications disclose niacinamide and ribose optimizing the nutritional content of the growth media. However, it was not recognized that combining niacinamide and a suitable saccharide at low pH in a skin care composition can provide improved skin barrier function and skin appearance benefits.

Typically, cosmetic compositions are formulated to have a slightly acidic to neutral pH (i.e., from 4.0-7.0) which is believed to improve the stability of certain ingredients in the composition (e.g., niacinamide, salicylates, and neutralized thickeners). However, formulating a skin care composition at a lower pH (e.g., 1.0-4.0) may bolster the acid mantle of the skin, provide flexibility in other types of skin agents that can be included in the composition, and/or provide an exfoliation benefit. Accordingly, it would be desirable to provide a low pH skin care composition that includes niacinamide and a suitable saccharide for improving skin barrier function and skin appearance.

SUMMARY

Disclosed herein are compositions and methods for improving the barrier function and/or appearance of skin. The methods utilize a topical skin care composition comprising an effective amount of niacinamide and a suitable saccharide; a pH of less than 4.0; and a dermatologically acceptable carrier. The saccharide in the composition can be a triose, tetrose, pentose, hexose or heptose (e.g., ribose). The composition generally has a pH of less than 4.0 (e.g., about 2.5). Due the low pH of the composition, fatty alcohol thickeners are particularly suitable for modifying the viscosity and/or feel properties of the composition. The methods further include identifying a target portion of skin in need of treatment and applying the composition thereto for a treatment period. The treatment period is sufficient for the niacinamide and saccharide in the composition to improve skin barrier function and/or skin appearance.

DETAILED DESCRIPTION

Niacinamide and various saccharides are common ingredients in some skin care compositions. However, when skin care compositions include niacinamide, they are generally formulated at a pH of greater than 4.0 for ingredient stability. One reason for this is that niacinamide can form complexes with other ingredients in a skin care composition at low pH, which reduces the bioavailability of the niacinamide. Surprisingly, it has now been discovered that low pH skin care compositions comprising niacinamide and a suitable saccharide such as ribose demonstrate improved skin care benefits compared to their higher pH counterparts. In particular, these low pH skin care compositions exhibit an increased ability to improve skin barrier function, reduce the size of hyperpigmented spots, and reduce skin yellowness, sallowness, and dullness.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"Apply" or "application", as used in reference to a composition, means to apply or spread the compositions of the present invention onto a human skin surface such as the epidermis.

"Cosmetic" means providing a desired visual effect on an area of the human body. The visual cosmetic effect may be temporary, semi-permanent, or permanent.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. For example, an effective amount of niacinamide and ribose is an amount sufficient to improve the barrier function of skin, improve the appearance of a hyperpigmented spot, and/or reduce the sallow appearance of skin.

"Hyperpigmented" and "hyperpigmented spot" mean a localized portion of skin with relatively high melanin content. Examples of hyperpigmented spots include, but are not limited to age spots, melasma, chloasma, freckles, post-inflammatory hyperpigmentation, sun-induced pigmented blemishes, and the like.

"Improve the appearance of" means providing a measurable, desirable change or benefit in male and/or female skin appearance, which may be quantified, for example, by a reduction in the Spot Area Fraction of a hyperpigmented spot and/or a decrease in b* value of sallow skin. Exemplary methods for determining improvements in appearance are described in more detail below.

"L*a*b*" refers to the commonly recognized color space specified by the International Commission on Illumination ("CIE"). The three coordinates represent (i) the lightness of the color (i.e., L*=0 yields black and L*=100 indicates diffuse white), (ii) the position of the color between magenta and green (i.e., negative a* values indicate green while positive a* values indicate magenta) and (iii) the position of the color between yellow and blue (i.e., negative b* values indicate blue and positive b* values indicate yellow).

"Low pH," as used herein, refers to cosmetic compositions that have a pH of less than 4.0, but typically greater than 1.0. A suitable method of determining the pH of a composition is described in more detail below.

"Saccharide" means a sugar. Saccharides herein can be mono-, di-, oligo-, or polysaccharides; sugar acids; sugar derivatives; or modified sugars.

"Safe and effective amount" means an effective amount of an ingredient that is low enough to avoid serious side effects (within the scope of sound medical judgment).

"Sallow," when referring to the appearance of skin herein, means an unusual yellow or pale skin tone, with regard to a particular individual, which is commonly associated with an unhealthy state. Sallow-appearing skin can be diagnosed objectively (e.g., with a color value such as L* or b*) or subjectively (e.g., by a skin care professional or consumer).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Skin tone agent" means a skin care active that can improve the appearance of uneven skin tone, hyperpigmented spots and/or overall basal skin tone (e.g., by lightening or reducing yellowness in sallow-looking skin). Skin tone agents may act via a variety of mechanisms, including, without limitation, acting as a lightening agent, anti-glycation agent, or pigmentation reduction agent.

"Skin tone" means the overall appearance of basal skin color or color evenness. Skin tone is typically characterized over a larger area of the skin. The area ideally may be than 100 mm$^2$, but larger areas are envisioned such as the entirety of the facial skin or other bodily skin surfaces (e.g., arms, legs, back, hands, neck, chest and abdomen). Skin tone can be measured by image analysis. For example, overall lightness can be measured by L* coordinate in L*a*b* color space (International Commission on Illumination). Chromophore mapping such as melanin mapping and melanin concentration may be used as an indicator of overall skin tone. Mean melanin may be calculated from the chromophore map data. Additionally, skin tone evenness can be determined by melanin evenness (e.g., standard deviation) which also may be calculated from the chromophore map data.

"Treatment period," as used herein, means the length of time and/or frequency that a material or composition is applied to a target skin surface.

Cosmetic Compositions

The compositions herein are intended for topical application to skin. The present compositions may be used to treat a variety of skin conditions such as, for example, skin conditions associated with or caused by inflammation; sun damage; ageing (intrinsic or extrinsic); hyperpigmentation (e.g., age spots); seborrheic keratosis; actinic keratosis; UV exposure; skin sallowness or yellowness; skin dullness; skin redness; sebum secretion; rough texture, wrinkles, compromised skin barrier (e.g., dry skin); contact dermatitis; atopic dermatitis; eczema; keratinization disorders; psoriasis; wound healing; and the like.

These cosmetic compositions herein comprise a safe and effective amount of niacinamide (CAS#98-92-0), sometimes referred to as nicotinamide or vitamin $B_3$, and a suitable saccharide. Non-limiting examples of saccharides that may be suitable for use herein include trioses such as glyceraldehyde and dihydroxyacetone; tetroses such as erythrose, threose, erythrulose; pentoses such as ribose, arabinose, ribulose, xylulose, xylose, lyxose, deoxyribose, dibulose, ribonic acid, and ribaric acid; hexoses such as allose, altrose, glucose, galactose, mannose, fructose, idose, talose, psicose, sorbose, tagatose, gulose, fucose, rhamnose, glucuronic acid, aldose, aldonic acid, glucaric acid, gularic acid, galactaric acid, galacturonic acid; heptoses such as sedoheptulose; nonoses such as neuraminic acid; saccharide derivatives such as ribulose 5-phosphate, xylulose 5-phosphate, ribose 5-phosphate, sedoheptulose 7-phosphate, glyceraldehyde 3-phosphate, fructose 6-phosphate, erythrose 4-phosphate, glucose 6-phosphate, 6-phosphoglucono-δ-lactone, 6-phosphogluconate, dihydroxyacetone phosphate, fructose 1,6-bisphosphate; and modified saccharides such as N-acetylglucosamine, N-acetylgalactosamine, and glucosamine. A particularly suitable saccharide for use herein is RIB OXY brand ribose available from Lucas Meyer Cosmetics, France. The niacinamide and/or saccharide may be present at an amount of from 0.05%, 0.5%, 1%, 2%, 3%, 4% or 5% to 20%, 15%, 10%, 8% or 6%.

The cosmetic compositions herein are formulated to have a low pH (e.g., 1.0 to 4.0, 1.5 to 3.5, 2.0 to 3.0, or even about 2.5). The cosmetic compositions herein may be provided in various product forms that include, but are not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. The cosmetic composition form may follow from the particular dermatologically acceptable carrier chosen, if present in the composition. The cosmetic compositions herein may be made using conventional methods of making such compositions.

Dermatologically Acceptable Carrier

The compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil or oil-in-water). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s). Emulsions may also contain an emulsifier, e.g., from about 1% to about 10% or from about 2% to about 5% based on the weight of the carrier. Emulsifiers may be nonionic, anionic or cationic. Some suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986), each incorporated herein by reference.

The carrier may contain one or more dermatologically acceptable, hydrophilic diluents. As used herein. "diluent" includes materials in which the niacinamide and/or saccharide can be dispersed, dissolved, or otherwise incorporated. Hydrophilic diluents include water, organic hydrophilic diluents such as lower monovalent alcohols (e.g., C1-C4) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Thickeners

In some instances, it may be desirable to use thickeners that tolerate a lower range of pH. For example, neutralized thickeners may not impart the desired thickening or feel properties to the composition at low pH. On the other hand, fatty alcohols such as cetyl alcohol and stearyl alcohol are generally stable at low pH, and thus particularly suited for use in the low pH compositions herein. Accordingly, the present compositions may be free or substantially free of neutralized thickeners and/or may have from 0.1% to 10% (e.g., from about 0.5% to about 8%, from about 1.0% to about 5%, or even from about 2% to about 4%) of a fatty alcohol thickener.

Sunscreen Actives

In some instances, it may be desirable to include one or more sunscreen actives in the present composition. The compositions of the subject invention may comprise one or more sunscreen actives (or sunscreen agents) and/or ultraviolet light absorbers. Herein, "sunscreen active" includes both sunscreen agents and physical sunblocks. Sunscreen actives and ultraviolet light absorbers may be organic or inorganic. Examples of suitable sunscreen actives and ultraviolet light absorbers are disclosed in Personal Care Product Council's International Cosmetic Ingredient Dictionary and Handbook, Thirteenth Edition, as "sunscreen agents." Particularly suitable sunscreen actives are 2-ethylhexyl-p-methoxycinnamate (commercially available as PARSOL™ MCX), 4,4'-t-butyl methoxydibenzoyl-methane (commercially available as PARSOL™ 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-trimethylcyclohexylsalicylate, menthyl anthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof. The composition may include from about 1% to about 20% or even from about 2% to about 10% by weight of the composition, of the sunscreen active and/or ultraviolet light absorber. Exact amounts will vary depending upon the chosen sunscreen active and/or ultraviolet light absorber and the desired Sun Protection Factor (SPF), and are within the knowledge and judgment of one of skill in the art.

Other Optional Ingredients.

The present composition may optionally include one or more additional ingredients commonly used in cosmetic compositions (e.g., colorants, skin tone agents, skin anti-aging agents, anti-inflammatory agents, sunscreen agents, emulsifiers, buffers, rheology modifiers, combinations of these and the like), provided that the additional ingredients do not undesirably alter the skin barrier and appearance benefits provided by the present composition. In some instances, it may be desirable to select skin tone agents that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition. The additional ingredients, when incorporated into the composition, should be suitable for use in contact with human skin tissue without undue toxicity, incompatibility, instability, allergic response, and the like. Some nonlimiting examples of additional ingredients which may be suitable for use herein are described in U.S. Publication Nos. 2002/0022040; 2003/0049212; 2004/0175347; 2006/0275237; 2007/0196344; 2008/0181956; 2010/00092408; 2008/0206373; 2010/0239510; 2010/0189669; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

Methods of Use

The present method includes identifying a target portion of skin (e.g., a facial skin surface such as the forehead, perioral, chin, periorbital, nose, and/or cheek) in need of treatment and applying a low pH composition comprising an effective amount of niacinamide and a suitable saccharide (e.g., ribose) to the target portion of skin. In some instances, the target portion of skin may appear sallow and/or include a hyperpigmented spot. In some instances, the target portion of skin may be skin where an improvement in skin barrier function is desired (e.g., dry facial skin). In some instances, the target portion of skin may not exhibit the characteristics of an undesirable skin condition, but a user (e.g., a relatively young user) may still wish to target such an area of skin if it is one that typically develops the undesirable condition later in life (e.g., skin surfaces that are typically not covered by clothing, such as facial skin surfaces, hand and arm skin surfaces, foot and leg skin surfaces, and neck and chest skin surfaces). In this way, the present compositions may be used in a preventative capacity. The composition may be applied to the target skin portion and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed.

The treatment period is ideally of sufficient time for the niacinamide and the saccharide present in the low pH composition to improve the barrier function and/or appearance of a target portion of skin. For example, TEWL, SAF, skin tone lightness, and/or skin tone yellowness in the target portion of skin may improve by at least 5% or more. The treatment period may last for at least 1 week (e.g., about 2 weeks, 4 weeks, 8 weeks, or even 12 weeks). In some instances, the treatment period will extend over multiple months (i.e., 3-12 months) or multiple years. In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a hyperpigmented spot or portion thereof) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Imaging Method

This method provides a means for capturing a reproducible and analyzable image for determining L*a*b* values and Spot Area Fraction. It is to be appreciated that any suitable image capture device along with imaging software and other associated ancillary equipment (e.g., computer and lights) which are equivalent to those described in this method may be used. The imaging system in this method incorporates a FUJI-S2 Pro brand CCD SLR digital camera which delivers a 6 megapixel uncompressed image (BMP) and a raw image file (RAF). Prior to taking a photograph, the test subject is illuminated with a JTL 1000W flash through two linear polarizers in crossed axis orientation. A chart containing Munsell Color Standard Neutral N2-N9.5 are captured in every image for standardization and color correction purposes.

In preparation for image capture, test subjects are required to wash their faces and wait for at least 15 minutes to let their face dry. The hair of the subject is covered with a hairnet and the head and shoulders of the subject are covered with a black cloth. All jewelry that can be seen in an image area of interest is removed. The subjects are equilibrated in a control room at 20-25° C. and 40-60% relative humidity for 30 minutes. Next, each subject is suitably positioned, in front of the camera and one or more images of each side of the face are captured. The captured image(s) are then processed by converting the raw image to a .jpg file format.

Next, the .jpg format image is analyzed by a computer with suitable image analysis software. In some instances, it may be desirable to analyze only a portion of the image (i.e., a region of interest ("ROI")). The ROI may be "masked" using suitable image editing software such as Photoshop® or Image J® brand software. The masked region can then be isolated and analyzed as a separate image. It is to be appreciated that the image need not necessarily be masked for suitable analysis, and in some instances the entire image may be analyzed. In some instances, it may be desirable to reduce the size of the image, mask and/or region of interest by several pixels (e.g., between 5 and 15 pixels) around the outer edge of the image where shadowing may occur.

Since color may be perceived as being relative, depending on, for example, which instruments and/or imaging system is used, it can be important to color correct the image or region of interest for each subject using a suitable color correction technique (e.g., according to International Color Consortium standards and practices), which helps make the color determination by the system less instrument specific. The RGB values in the captured images, which are device dependent, are converted to L*a*b* values. The L*a*b* values can be calculated using a suitable RGB conversion tool (e.g., software installed on the computer or a suitable conversion tool found online). The conversion from RGB values to L*a*b* values can be performed on the entire image, a ROI, or on one or more individual pixels. The resulting L*a*b* values may be averaged to provide average values for the image or a region of interest.

Spot Area is the total area of spots (in pixels) detected in the desired ROI. Spots are detected by comparison of localized detection of lower gray density objects from higher gray density background in the desired channel of the RGB color space. The detected objects are further classified by shape and size.

Spot Area Fraction may be represented by the equation below.

$$SAF(\%) = \frac{\text{Cummulative spot area within the } ROI * 100}{\text{Area of the } ROI}$$

The change in SAF from baseline ("ΔSAF") is the difference between the spot area (normalized to the ROI) after a treatment period and the spot area (normalized to the ROI) just prior to treatment (e.g., $SAF_{final} - SAF_{baseline}$). A lower percentage reflects a reduction in total spot area. ΔSAF is used to statistically calculate and compare product treatment effects (e.g., composition vs. vehicle control) at each time point.

EXAMPLE

This example demonstrates the ability of a low pH skin care composition comprising niacinamide and a saccharide (ribose) to treat various skin conditions. In particular, this example demonstrates the ability of the present skin care compositions improve skin barrier function and improve the appearance of hyperpigmented spots and sallow looking skin.

Approximately 35 Caucasian female test subjects aged 25-60 were selected for each leg of a 9-week, randomized, double-blind, round-robin, split-face study. The study included a 1 week normalization period and an 8 week test period. Prior to application of a composition, the test subjects washed their face with OLAY DEEP PURIFY CLEANSER brand facial cleanser available from The Procter & Gamble Co., Cincinnati, Ohio. Approximately 0.5 g of the appropriate composition was applied to each side of the test subject's face twice per day (morning/evening) during the test period (forehead to jawline 4 mg/cm²). TEWL measurements were taken at the start of the test period (baseline) and after 2, 4, 6 and 8 weeks of treatment. Digital images were captured and analyzed for changes in L*, b*, and SAF at the start of the test period (baseline) and at weeks 2, 4 and 8 according the Imaging Method described above. The data were statistically analyzed with a known Mixed Model (e.g., available from SAS Institute, Cary, N.C., U.S.A.) for repeated measures with the subject effect fitted as random, and the other effects (treatment, side (left and right), week, treatment-by-week interaction, age, baseline) fitted as fixed. Values are considered statistically significant if the p-value is less than or equal to 0.05.

The compositions tested in this example are shown in Table 1 below. Composition A is a conventional skin care chassis, and is used as the control. Composition A differs from the test composition with regard to thickeners and a few other optional ingredients, but these ingredients should not affect the properties measured in these examples. Composition B is the low pH test composition. Composition C is a higher pH comparative composition (i.e., the higher pH counterpart to composition A). The pH of the compositions was measured by using an ORION brand 525A pH meter (or equivalent) equipped with a flat surface electrode/probe (VWR Cat. No. 89231-584). The probe of the pH meter is immersed directly into a neat sample of the composition. The compositions were prepared using conventional methods of making skin compositions.

TABLE 1

| Ingredient | % | | |
| --- | --- | --- | --- |
| | A | B | C |
| Water | QS | QS | QS |
| Glycerin | 10.0000 | 10.0000 | 10.0000 |
| Disodium EDTA | 0.1000 | 0.1000 | 0.1000 |
| Tocopheryl acetate | 0.5000 | 0.5000 | 0.5000 |
| Isohexadecane | 3.0000 | 3.0000 | 3.0000 |
| Polyacrylamide (and) C13-14 Isoparaffin (and) Laureth-7[1] | 2.000 | — | — |
| Isopropyl Isostearate | 1.3300 | 1.3300 | 1.3300 |
| Polymethylsilsesquioxane | 0.2500 | 2.0000 | 2.0000 |
| Behenyl Alcohol | 0.4000 | 0.4000 | 0.4000 |
| Ethylparaben | 0.2000 | 0.2000 | 0.2000 |
| Propylparaben | 0.1000 | 0.1000 | 0.1000 |
| Cetyl Alcohol | 0.3200 | 0.3200 | 0.3200 |

TABLE 1-continued

| Ingredient | % | | |
| --- | --- | --- | --- |
| | A | B | C |
| Cetearyl Glucoside, Cetearyl Alcohol | 0.2000 | — | — |
| Stearyl Alcohol | 0.4800 | 2.0000 | 2.0000 |
| Steareth-2 | — | 1.000 | 1.000 |
| Steareth-21 | — | 0.800 | 0.800 |
| Distearyldimonium Chloride | — | 1.000 | 1.000 |
| Polyethylene[1] | — | 1.5000 | 1.5000 |
| Panthenol | 1.0000 | 0.5000 | 1.0000 |
| Niacinamide | — | 2.1000 | 2.1000 |
| D-ribose[2] | — | 2.5900 | 2.5900 |
| Hydrochloric Acid, >25% and fuming (6N) | — | 2.5000 | — |
| Benzyl Alcohol | 0.2500 | 0.2500 | 0.2500 |
| Dimethicone and Dimethiconol[3] | 2.0000 | 2.0000 | 2.0000 |
| pH | 5.5 | 2.8 | 5.0 |

[1]SEPIGEL (Sepic, France)
[2]EMULGLADE PL 68/50 (BASF, Germany)
[3]MICROTHENE FN 510-00 (Equistar Chemicals, Texas).
4. RIBOXYL (Lucas Meyer Cosmetics, France)
5. DOW CORNING 1503 fluid (Dow Corning, Michigan)

Skin Barrier Function—TEWL

Figure 1:
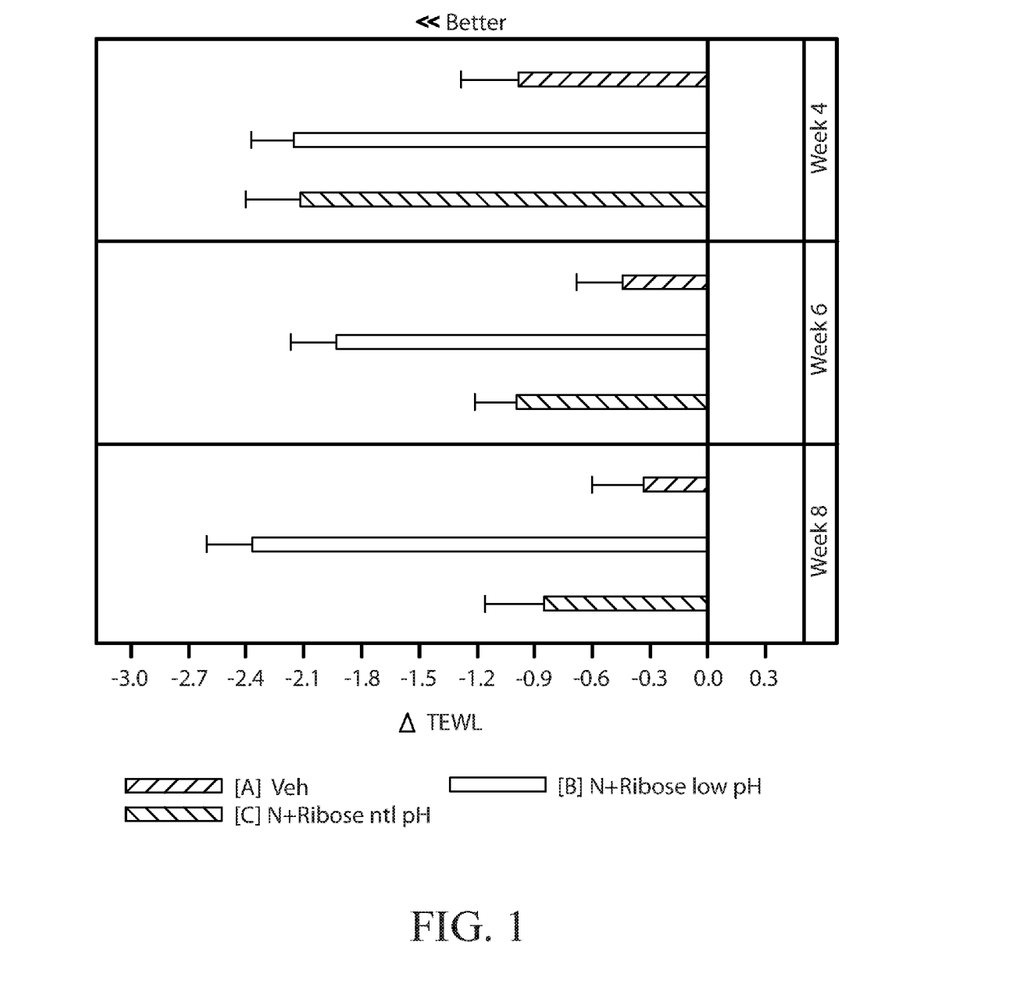
FIG. 1. is a chart illustrating a change in trans-epidermal water loss.

Skin barrier function in this example is quantitated by measuring the trans-epidermal water loss ($g/m^2/hr$) of skin areas treated with one of the compositions from Table 1. TEWL is a well-known indicator of skin barrier function, and reducing TEWL is generally believed to correspond to an improvement in skin barrier function. In this example, TEWL was measured using a VAPOMETER brand moisture detector (available from Delfin Technologies Ltd, Finland) according to the manufacturer's instructions, but it is to be appreciated that an equivalent device could also be used. The results of the TEWL measurements are summarized below in Table 2 and illustrated in FIG. 1. The results of this test demonstrate that a low pH skin care composition of niacinamide and ribose improves skin barrier function better than the vehicle control at weeks 4, 6, and 8 and the corresponding high pH composition (C) at weeks 6 and 8. In some instances, the compositions herein may reduce TEWL by at least 5% (e.g., at least 10%, 15%, 20%, 25%, or more).

TABLE 2

| | | | TEWL | | | |
| --- | --- | --- | --- | --- | --- | --- |
| | N | Composition | TEWL | ΔTEWL from baseline | p-value (vs. baseline) | p-value (vs. control) | p-value (vs. C) |
| Baseline | | — | 12.984 | — | — | — | — |
| Week 2 | 35 | Composition A | 12.077 | −0.907 | 0.0002 | | |
| Week 4 | 35 | (control) | 11.996 | −0.988 | 0.0010 | — | — |
| Week 6 | 34 | | 12.539 | −0.445 | 0.0585 | — | — |
| Week 8 | 33 | | 12.653 | −0.331 | 0.2237 | — | — |
| Week 2 | 35 | Composition C | 11.542 | −1.441 | <0.0001 | 0.1162 | |
| Week 4 | 35 | (high pH) | 10.863 | −2.121 | <0.0001 | 0.0023 | — |
| Week 6 | 35 | | 11.989 | −0.995 | <0.0001 | 0.0579 | — |
| Week 8 | 34 | | 12.129 | −0.855 | 0.0050 | 0.1497 | — |
| Week 2 | 35 | | 10.973 | −2.011 | <0.0001 | <0.0001 | 0.1276 |
| Week 4 | 35 | Composition B | 10.832 | −2.152 | <0.0001 | 0.0004 | 0.9185 |
| Week 6 | 34 | (low pH) | 11.060 | −1.924 | <0.0001 | <0.0001 | 0.0018 |
| Week 8 | 34 | | 10.614 | −2.370 | <0.0001 | <0.0001 | <0.0001 |

Improving the Appearance of a Hyperpigmented Spot—Spot Area Fraction

Figure 2:
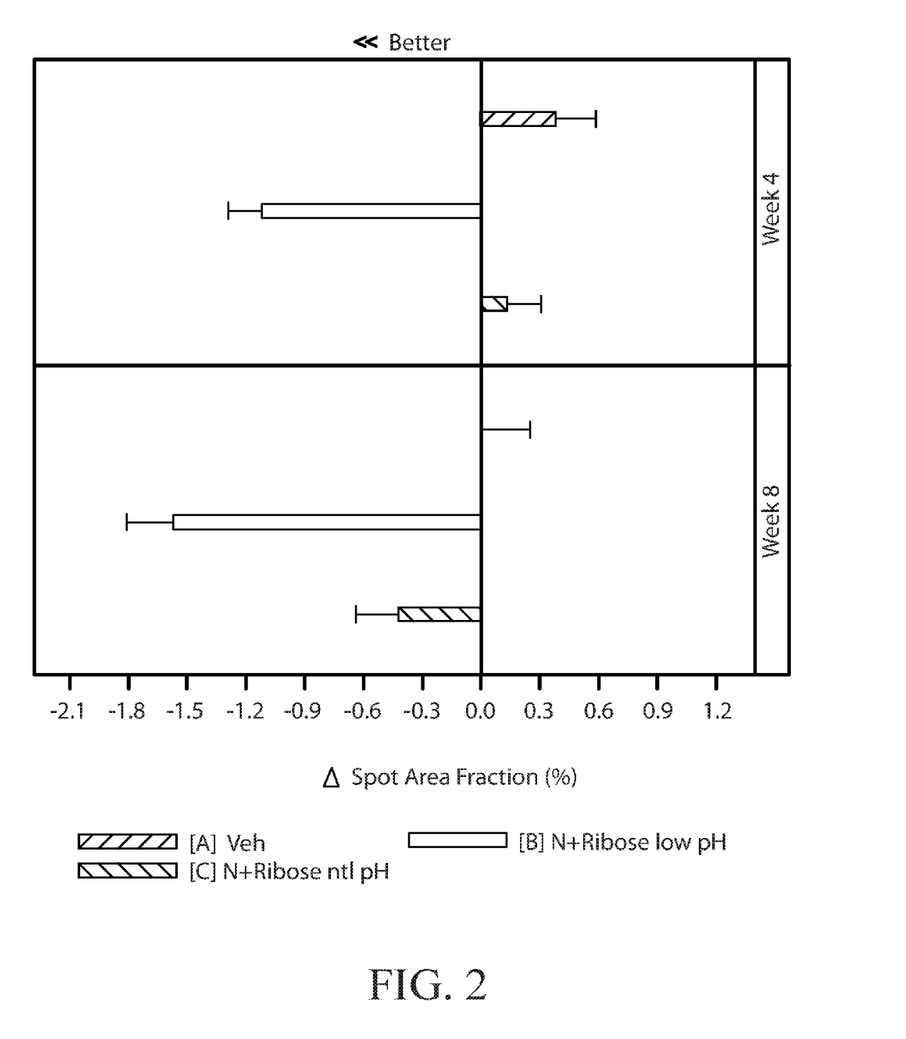
FIG. 2 is a chart illustrating a change in spot area fraction.

In this example, the improvement in the appearance of skin hyperpigmentation is quantitated by measuring the change in spot area fraction ("SAF") of a hyperpigmented portion of skin treated with one of the compositions used in the study. SAF is a well-known method of quantitating the improvement in appearance of a hyperpigmented portion of skin. A reduction in SAF corresponds to an improvement in appearance. In this example, SAF was measured according the imaging method described above. The results of the SAF measurements are summarized below in Table 3 and illustrated in FIG. 2. The results of this test demonstrate that a low pH skin care composition of niacinamide and ribose improves the appearance of hyperpigmented spots better than the vehicle control and the corresponding high pH composition after 4 weeks of treatment. In some instances, the compositions herein may reduce SAF by at least 5% (e.g., at least 10%, 15%, 20%, 25%, 30%, 35%, 40%, 45%, 50%, or more).

TABLE 3

SAF

|  | N | Composition | SAF [%] | ΔSAF from baseline | p-value (vs. baseline) | p-value (vs. control) | p-value (vs. C) |
|---|---|---|---|---|---|---|---|
| Baseline |  | — | 9.179 | — | — | — | — |
| Week 2 | 35 | Composition A | 9.141 | −0.038 | 0.8338 |  |  |
| Week 4 | 35 | (control) | 9.557 | 0.378 | 0.0613 | — | — |
| Week 8 | 34 |  | 9.180 | 0.001 | 0.9972 | — | — |
| Week 2 | 35 | Composition C | 9.286 | 0.107 | 0.5274 | 0.5182 |  |
| Week 4 | 35 | (high pH) | 9.312 | 0.133 | 0.4363 | 0.2665 | — |
| Week 8 | 35 |  | 8.754 | −0.425 | 0.0415 | 0.1108 | — |
| Week 2 | 35 | Composition B | 8.543 | −0.635 | <0.0001 | 0.0050 | 0.0006 |
| Week 4 | 35 | (low pH) | 8.065 | −1.114 | <0.0001 | <0.0001 | <0.0001 |
| Week 8 | 34 |  | 7.613 | −1.566 | <0.0001 | <0.0001 | <0.0001 |

Improving the Appearance of Sallow Looking Skin—ΔL* and Δb*

Figure 3:
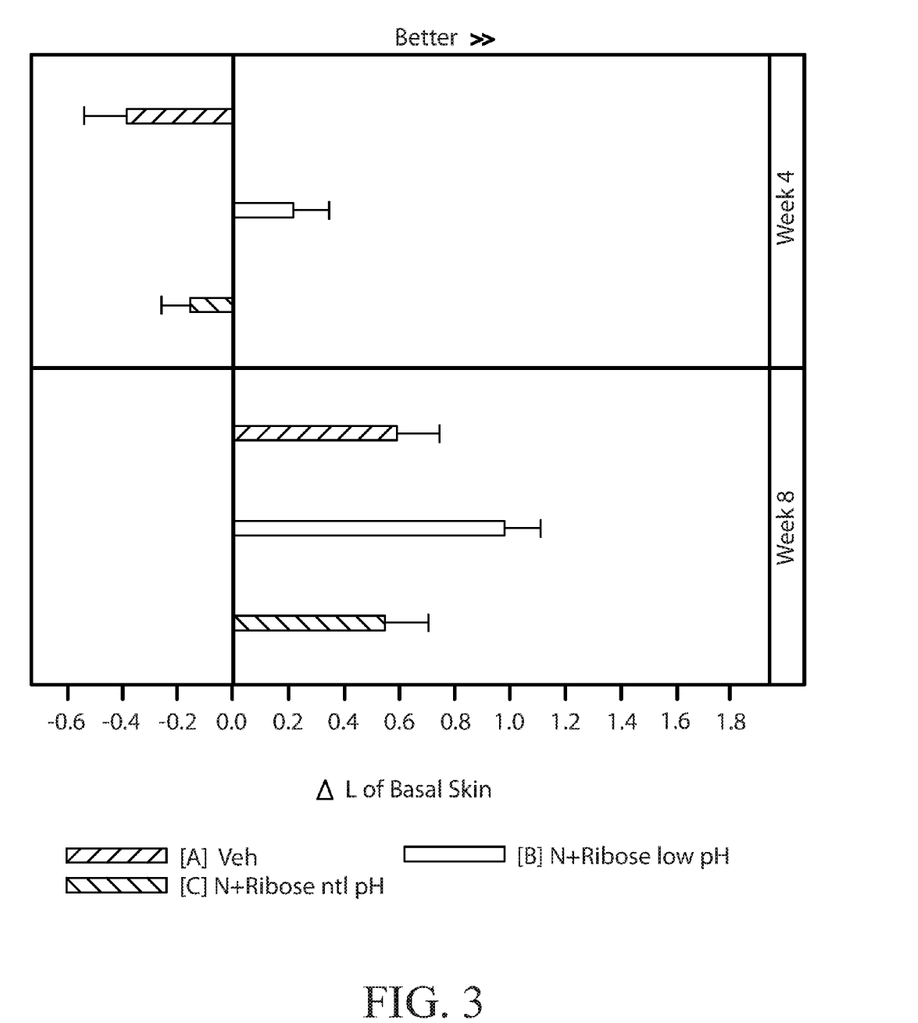
FIG. 3 is a chart illustrating a change in skin tone lightness.
Figure 4:
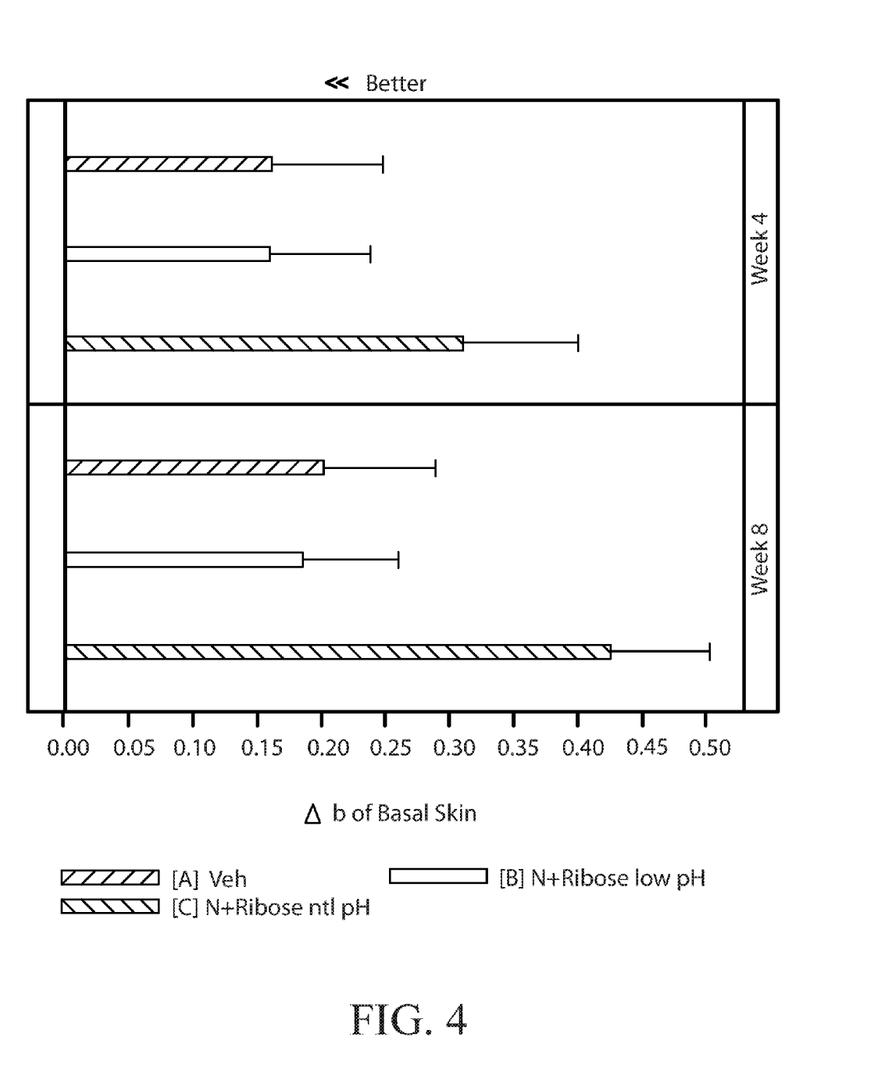
FIG. 4 is a chart illustrating a change in skin tone yellowness.

In this example, the improvement in the appearance of sallow looking skin is quantitated by measuring the change in lightness (ΔL*) and yellowness (Δb*) of portions of skin treated with one of the compositions used in the study. Measuring the changes in lightness and yellowness are commonly used to quantitate the improvement in appearance of sallow looking skin. An increase in lightness and/or a decrease in yellowness correspond to an improvement in the appearance of sallow-looking skin. In this example, ΔL* and Δb* were measured according the imaging method described above. The results of the ΔL* and Δb* measurements are summarized below in Tables 4 and 5 and illustrated in FIGS. 3 and 4. The results of this test demonstrate that a low pH skin care composition of niacinamide and ribose improves the appearance of sallow skin better than the vehicle control and a corresponding high pH composition. In particular, the test composition lightened skin better than the vehicle control and the comparative composition after 4 weeks of treatment. Additionally, the test composition did not increase lightness any more than the vehicle control after 4 weeks of treatment, whereas the high pH composition appears to cause a substantial increase in yellowness. In some instances, the compositions herein may increase skin lightness (i.e., L*) and/or reduce yellowness (i.e., b*) by at least 5% (e.g., at least 10%, 15%, 20%, 25%, or more).

TABLE 4

Skin Lightness

|  | N | Composition | L*-value [—] | ΔL* from baseline | p-value (vs. baseline) | p-value (vs. control) | p-value (vs. C) |
|---|---|---|---|---|---|---|---|
| Baseline |  | — | 60.851 | — | — | — | — |
| Week 2 | 35 | Composition A | 60.749 | −0.102 | 0.2566 |  |  |
| Week 4 | 35 | (control) | 60.465 | −0.386 | 0.0108 | — | — |
| Week 8 | 34 |  | 61.438 | 0.588 | 0.0002 | — | — |
| Week 2 | 35 | Composition C | 60.677 | −0.174 | 0.0458 | 0.5464 |  |
| Week 4 | 35 | (high pH) | 60.696 | −0.154 | 0.1464 | 0.1447 | — |
| Week 8 | 35 |  | 61.401 | 0.550 | 0.0004 | 0.8397 | — |
| Week 2 | 35 | Composition B | 60.972 | 0.121 | 0.3227 | 0.0820 | 0.0193 |
| Week 4 | 35 | (low pH) | 61.069 | 0.218 | 0.0727 | 0.0002 | 0.0033 |
| Week 8 | 34 |  | 61.831 | 0.980 | <0.0001 | 0.0200 | 0.0089 |

TABLE 5

Skin Yellowness

|  | N | Composition | b*-value [—] | Δb* from baseline | p-value (vs. baseline) | p-value (vs. control) | p-value (vs. C) |
|---|---|---|---|---|---|---|---|
| Baseline |  | — | 17.515 | — | — | — | — |
| Week 2 | 35 | Composition A | 17.717 | 0.202 | 0.0049 |  |  |
| Week 4 | 35 | (control) | 17.676 | 0.161 | 0.0640 | — | — |
| Week 8 | 34 |  | 17.717 | 0.202 | 0.0200 | — | — |
| Week 2 | 35 | Composition C | 17.851 | 0.336 | <0.0001 | 0.1352 |  |
| Week 4 | 35 | (high pH) | 17.824 | 0.310 | 0.0006 | 0.1577 | — |
| Week 8 | 35 |  | 17.940 | 0.425 | <0.0001 | 0.0348 | — |
| Week 2 | 35 | Composition B | 17.841 | 0.327 | <0.0001 | 0.1951 | 0.9157 |
| Week 4 | 35 | (low pH) | 17.675 | 0.160 | 0.0392 | 0.9910 | 0.1536 |
| Week 8 | 34 |  | 17.700 | 0.185 | 0.0132 | 0.8608 | 0.0119 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical skin care composition, comprising:
   a. from about 0.01% to about 15% niacinamide;
   b. from about 0.01% to about 15% of a saccharide;
   c. a pH of less than 4.0; and
   d. a dermatologically acceptable carrier.

2. The composition of claim 1, wherein the saccharide is selected from pentoses and hexoses.

3. The composition of claim 2, wherein the saccharide is ribose.

4. The composition of claim 1, wherein the pH is between about 1.5 and 3.5.

5. The composition of claim 1, further comprising from about 0.1% to about 10% of a fatty alcohol thickener.

6. The composition of claim 1, further comprising at least one additional skin care active and a sunscreen agent.

7. A method of treating a skin condition, comprising:
   a. identifying a target portion of skin where treatment is desired; and
   b. topically applying a cosmetic composition to the target portion of skin during a treatment period, wherein the composition comprises
      i. an effective amount of niacinamide,
      ii. an effective amount of a saccharide,
      iii. a pH of less than 4.0, and
      iv. a dermatologically acceptable carrier,
   wherein the treatment period is sufficient for the niacinamide and saccharide to improve the skin condition.

8. The method of claim 7, wherein the skin condition is selected from inflammation, sun damage, ageing, hyperpigmentation, seborrheic keratosis, actinic keratosis, UV exposure, skin sallowness, skin yellowness, skin dullness, skin redness, sebum secretion, rough texture, wrinkles, compromised skin barrier, contact dermatitis, atopic dermatitis, eczema, keratinization disorders, psoriasis, and wound healing.

9. The method of claim 8, wherein the skin condition is hyperpigmentation and the treatment period is sufficient for the niacinamide and saccharide to reduce a spot area fraction (SAF) of a hyperpigmented spot by at least 2%.

10. The method of claim 8, wherein the skin condition is compromised skin barrier and the treatment period is sufficient for the niacinamide and saccharide to reduce the trans-epidermal water loss (TEWL) of the target portion of skin by at least 5%.

11. The method of claim 8, wherein the skin condition is skin dullness and the treatment period is sufficient for the niacinamide and saccharide to increase an L* value of the target portion of skin by at least 5%.

12. The method of claim 8, wherein the skin condition is skin yellowness and the treatment period is sufficient for the niacinamide and saccharide to decrease a b* value of the target portion of skin by at least 5%.

13. The method of claim 8, wherein the skin condition is skin sallowness and the treatment period is sufficient for the niacinamide and the saccharide to increase an L* value and decrease a b* value of the target portion of skin by at least 5%.

14. The method of claim 7, wherein the cosmetic composition includes from about 0.01% to about 15% niacinamide.

15. The method of claim 7, wherein the cosmetic composition includes from about 0.01% to about 15% of a saccharide.

16. The method of claim 7, wherein the composition further comprises a pH of less than 4.0.

17. The composition of claim 7, wherein the saccharide is ribose.

18. The composition of claim 7, further comprising from about 0.1% to about 10% of a fatty alcohol thickener.

19. The composition of claim 7, further comprising at least one additional skin care active and a sunscreen agent.

* * * * *